United States Patent [19]

Kaufman

[11] 4,269,852
[45] May 26, 1981

[54] 4'-SUBSTITUTED-4,5',8-TRIALKYLPSORALENS

[75] Inventor: Kurt D. Kaufman, Kalamazoo, Mich.

[73] Assignee: Thomas C. Elder, Inc., Hamilton, Ind.

[21] Appl. No.: 73,909

[22] Filed: Sep. 10, 1979

[51] Int. Cl.$^3$ .................. C07D 493/04; A61K 31/365
[52] U.S. Cl. .................................. 424/279; 260/343.21
[58] Field of Search .................. 260/343.21; 424/279, 424/59

[56] References Cited

U.S. PATENT DOCUMENTS

| 4,124,598 | 11/1978 | Hearst et al. ................ 260/343.21 |
| 4,169,204 | 9/1979 | Hearst et al. ................ 260/343.21 |

OTHER PUBLICATIONS

Hearst et al., (II) Chem. Abst. 87:78962f, 1977.
Dawber, J. Soc. Comet. Chem. 28–403 to 406, 1977.
Martins et al., Chem. Abst., vol. 81, 1974, 99676g.
Shen et al., Chem. Abst., vol. 88, 59494j.
Johnston et al., Chem. Abst., 87:147284a.
Isaacs et al., Chem. Abst., 86:135108n.

*Primary Examiner*—Henry R. Jiles
*Assistant Examiner*—Jane T. Fan
*Attorney, Agent, or Firm*—Gordon W. Hueschen

[57] ABSTRACT

The invention relates to 4,5',8-trialkylpsoralens, having a substituent on the 4' carbon atom which is selected from hydroxyalkoxyalkyl and hydroxyalkylaminoalkyl, which are characterized by enhanced photosensitizing activity, especially oral activity, including comparable maxima, early onset, and especially rapid decline, as well as low toxicity, when contrasted with psoralens of different structure.

15 Claims, No Drawings

4'-SUBSTITUTED-4,5',8-TRIALKYLPSORALENS

BACKGROUND OF INVENTION

1. Field of Invention

Psoralens, photochemotherapy, psoralens having enhanced photosensitizing activity for use in photochemotherapy.

2. Prior Art

Psoralens have been used for years as dermalphotosensitizing agents, e.g., in the treatment of vitiligo. Their topical and/or oral application, followed by irradiation with light, results in stimulation of melanin, thus producing a tanning effect. They have accordingly also been used for such cosmetic purpose. More recently, psoralens have been found useful in the photochemotherapeutic treatment of psoriasis, in which case they are administered orally or topically to the subject, whose skin is subsequently exposed to controlled ultraviolet radiation, as in a Psoralite (TM) apparatus. A high percentage of remissions of this disease have been effected in such manner.

The effectiveness of a psoralen for such uses and for such purpose is related to its ability to produce erythema upon the skin upon irradiation. Psoralens also have other uses, and their uses, as well as underlying rationale and theory, are partially elucidated in U.S. Pat. No. 4,124,598, and are otherwise well-known in the art from various preexisting publications.

With the increasing emphasis on photochemotherapeutic treatments for various purposes using psoralens and controlled application of ultraviolet light, the requirements for optimally-effective photosensitizing psoralens have become more apparent. To eliminate the necessity of excessive and perhaps dangerous ultraviolet light applications or dosages, maximum photosensitization is one obvious criterion. However, to eliminate excessive periods of waiting before photochemotherapy can be commenced, rapid onset of photosensitization upon topical or oral administration of the photosensitizing agent is also of significance. Perhaps an even more important criterion is rapid decline in photosensitizing activity of the photosensitizing agent after reaching maximum and/or effective photosensitization levels after administration. Obviously, if the photosensitization effect does not decline relatively rapidly, or at least within a reasonably limited period after maximization, a patient must be confined for uneconomic and undesirable periods after treatment so that photosensitization does not continue after the desired ultraviolet light treatment period, with the distinct danger of excessive and undesirable continuance of photochemotherapy because of exposure to normally-encountered light rays upon leaving the treatment area. Thus, the criteria of rapid onset, early maximization, and rapid decline of photosensitization effect have already become established as desirable criteria for the photosensitizing agent in this relatively new but rapidly-expanding field of photochemotherapy, certainly of equal importance as contrasted to the single previously-important criterion of high maximum photosensitization activity alone.

Although some psoralens, such as trimethylpsoralen (4,5',8-trimethylpsoralen or trioxsalen) are characterized by considerable topical activity, they have a diminished order of oral activity, or at least the oral activity is a modicum for purposes of practical photochemotherapeutic utilization. In contrast, 8-methoxypsoralen is characterized by significant oral activity. The psoralen compounds of U.S. Pat. Nos. 4,124,598 and 4,130,568 are also characterized structurally by the presence of an 8 carbon atom substituent, e.g., an 8-methoxy or 8-methyl substituent, which has heretofore apparently been considered desirable for substantial photosensitizing activity, whether oral or topical, of course along with other substituents present in the 4',4, and 5' positions, in those prior art psoralen compounds which have heretofore been found to have desired photochemotherapeutic activity.

OBJECTS OF THE INVENTION

It is an object of the invention to provide novel psoralen compounds. It is a further object to provide novel psoralen compounds which have enhanced characteristics when compared with psoralen compounds of different structure. It is an additional object to provide novel psoralen compounds having enhanced photosensitizing characteristics in accord with the foregoing stated criteria. It is a still further object to provide novel psoralen compounds having enhanced photosensitizing characteristics and relatively low toxicity, and of a structure differing essentially from known psoralen compounds, the advantageous properties of which could not be predicted on a basis of any known structure-activity relationships. Still other objects will be apparent to one skilled in the art and still additional objects will become apparent hereinafter from the following description and claims.

SUMMARY OF THE INVENTION

The present invention relates to 4,5',8-trialkylpsoralens, having a substituent on the 4' carbon atom which is selected from hydroxyalkoxyalkyl and hydroxyalkylaminoalkyl, which are characterized by enhanced photosensitizing activity, especially oral activity, including comparable maxima, early onset, and especially rapid decline, as well as low toxicity, when contrasted with psoralens of different structure. It is particularly concerned with 4'-R-4,5',8-triloweralkylpsoralens, wherein the 4'-R substituent is hydroxyloweralkoxyalkyl or hydroxyloweralkylaminoalkyl, and especially 4'-hydroxyloweralkoxymethyl-4,5',8-trimethylpsoralen, e.g, 4'-beta-hydroxyethoxymethyl-4,5',8-trimethylpsoralen, and 4'-(N-hydroxyloweralkyl)aminomethyl-4,5',8-trimethylpsoralen, e.g., 4'-(N-(beta-hydroxyethyl)aminomethyl)-4,5',8-trimethylpsoralen. It is to be noted that these compounds do not have the identical substituents as the prior art compounds trisoralen (4,5',8-trimethylpsoralen), 8-methoxypsoralen, or the compounds of U.S. Pat. Nos. 4,124,598 or 4,130,568. In particular, the 4' carbon atom substituent is uniquely present in the compounds of the invention, but absent from and unsuggested by any or all of the aforementioned reference compounds. These new compounds are characterized by excellent photosensitization activity according to the aforesaid various criteria, as well as relatively low toxicity.

The compounds of the invention have the formula:

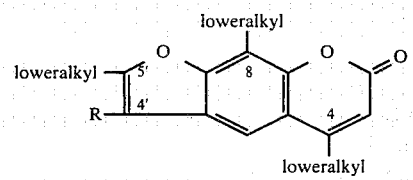

wherein R is hydroxyloweralkoxyalkyl or hydroxyloweralkylaminoalkyl, wherein loweralkyl is preferably methyl and R is preferably hydroxyethoxymethyl or hydroxyethylaminomethyl.

DETAILED DESCRIPTION OF THE INVENTION

The following preparations and examples are given by way of illustration only.

The starting materials for preparing the compounds of the present invention are known compounds. 4,5′,8-Trialkylpsoralens are well known. Trioxsalen is one example. The 4′-haloalkyl derivatives thereof are also known compounds. The 4′-chloroalkyl derivatives are disclosed in U.S. Pat. No. 4,124,598 and in the publication of Isaacs, Shen, Hearst and Rapoport in Biochem. 16, 1058–1064 (1977). The 4′-bromoalkyl compounds are prepared in the same manner. Such 4,5′,8-trialkyl derivatives are made in the manner disclosed in U.S. Pat. No. 4,124,598. The 4′-hydroxyalkoxyalkyl compounds and the 4′-hydroxyalkylaminoalkyl compounds of the invention are prepared by respectively reacting a selected di or polyhydroxyalkane, e.g., a glycol, or aminoalkanol, with the selected 4′-haloalkyl-4,5′,8-trialkylpsoralen starting material, in each case to produce the selected 4′-hydroxyalkoxyalkyl 4,5′,8-trimethylpsoralen or 4′-hydroxyalkylamino alkyl-4,5′,8-trimethylpsoralen.

Thin layer chromatography was done on Analtech, Silica Gel GF$_{254}$, 250 micron, glass-backed slides. NMR were run on a Perkin Elmer Model R-24B. All melting points are corrected.

4′-Chloromethyl-4,5′,8-trimethylpsoralen. Chloromethyl methyl ether (200 ml.) was added to a solution of 4,5′,8-trimethylpsoralen (29.36 g., 0.13 mole) in glacial acetic acid (3 l.) at room temperature. After 51 hours, the solution was refrigerated (−5° C.) for eight hours, allowed to thaw until the acetic acid had melted, and filtered to obtain crystals that weighed 13.63 g. (38.3% yield) and had m.p. 211°–212° C. (lit.: 215°–217° C.) after drying over KOH, followed by a vacuum oven at 80° C.

The corresponding 4′-bromomethyl compound is prepared in the same manner using bromomethyl methyl ether.

4′-BETA-HYDROXYETHOXYMETHYL-4,5′,8-TRIMETHYLPSORALEN

A solution of 4′-chloromethyl-4,5′,8-trimethylpsoralen (3 g., 0.01 mole) in ethylene glycol (750 ml.) was kept at 90° C. for four hours and then distilled at 90° C./1 torr. Recrystallization of the residue from water gave colorless crystals, 2.26 g. (68% yield), m.p. 151°–152° C., nmr (CDCl$_3$); δ 2.4 (s, 9H, CH$_3$); δ 3.5–3.9 (multiplet, 4H, CH$_2$CH$_2$); δ 4.6 (s, 2H, CH$_2$); δ 6.1 (s, 1H, C$_3$-H); δ 7.4 (s, 1H, C$_5$-H).

Anal. Calcd. for C$_{17}$H$_{18}$O$_5$: C, 67.54; H, 6.00. Found: C, 67.26; H, 6.16.

4′-GAMMA-HYDROXYPROPOXYMETHYL-4,5′,8-TRIMETHYLPSORALEN

In the same manner as given in the foregoing, but starting from 4′-bromomethyl-4,5′,8-trimethylpsoralen and 1,3-propylene glycol, the title compound is produced.

4′-DELTA-HYDROXYBUTOXYMETHYL-4,5′,8-TRIMETHYLPSORALEN

In exactly the same manner but starting from 1,4-butanediol instead of propylene glycol, the title compound is produced.

4′-BETA,GAMMA-DIHYDROXYPROPOXYMETHYL-4,5′,8-TRIMETHYLPSORALEN

In the same manner as given in the foregoing, but starting from 4′-bromomethyl-4,5′,8-trimethylpsoralen and glycerine, the title compound is produced.

4′-BETA-HYDROXYETHOXYETHYL-4,5′,8-TRIETHYLPSORALEN

In the same manner as given in the foregoing, but starting from 4′-chloroethyl-4,5′,8-triethylpsoralen and ethylene glycol, the title compound is produced.

In the same manner as given in the foregoing, other variations in selection of starting materials are productive of still other 4′-hydroxyloweralkoxyloweralkyl-4,5′,8-triloweralkylpsoralens within the scope of the invention in which one, two, three, or all of the loweralkyl groups present in the molecule are varied. As used herein, the term "loweralkyl" comprehends such straight or branched radicals or groups having one to eight carbon atoms, preferably one to four carbon atoms, inclusive, such as methyl, ethyl, propyl, isopropyl, butyl, and the like. "Loweralkoxy" has the formula loweralkyl-O and, when present in the 4′ position as part of the hydroxyloweralkoxyloweralkyl group, loweralkoxy will also be substituted by one or more hydroxy groups, as illustrated by the foregoing examples, depending upon the di or polyhydroxyloweralkane, e.g., glycol, starting material employed.

4′-(N-(BETA-HYDROXYETHYL)AMINOMETHYL)-4,5′,8-TRIMETHYLPSORALEN

4′-chloromethyl-4,5′,8-trimethylpsoralen (2.00 g, 7.2 mmoles) was dissolved in aminoethanol (25 ml, 414 mmoles) at 90° C. The stirred solution was heated for two hours at 90° C. and the aminoethanol was stripped off using a rotary evaporator operated by a high vacuum pump. To the residue was added 10 ml of 5% HCl which made the suspension red to pH paper. About 4 ml of 20% NaOH was then added until the suspension was blue to pH paper. The precipitate was collected and washed with 10% NaCl until the filtrate was non-alkaline to pH paper (3×10 ml washes). Then the precipitate was washed with 10 ml of water, and dried in a vacuum oven (<1 mm Hg, 80° C.) to obtain a crude yield of 1.978 g (91% yield), melting point 168° C.–173° C. Recrystallization from n-butanol gave colorless crystals, 1.204 g (56% yield), melting point 174° C.–177° C. TLC analysis using benzene:methanol::1:1, showed product contaminated with starting material. Another recrystallization from n-butanol gave 0.904 g (42% yield), melting point 174.5° C. to 177.5° C. TLC analysis using benzene:methanol::3:1, showed only a trace of starting material remaining. NMR(CDCl$_3$)δ2.05 (s,2,N—H+O—H), 2.45(d,9, J=3 Hz, C4,5′,8- methyls),2.80(t,2, J=6 Hz, CH$_2$—O), 3.65(t,2, J=6 Hz, C—CH$_2$—N), 3.85(s,2,4'-CH$_2$—N); 6.09(s,1,C3-H), 7.49(s,1, C5-H).

Anal. Calcd for C$_{17}$H$_{19}$NO$_4$: C, 67.76; H, 6.36; N, 4.65. Found: C, 67.67; H, 6.42; N, 4.33.

4'-(N-(GAMMA-HYDROXYPROPYL)AMINOMETHYL)-4',5',8-TRIMETHYLPSORALEN

In the same manner as given in the foregoing, but starting from 3-aminopropanol instead of aminoethanol, the title compound is produced.

4'-(N-(BETA-HYDROXYETHYL)-(N-METHYL)-AMINOMETHYL)-4',5',8-TRIMETHYLPSORALEN

In the same manner as given in the foregoing, but starting from N-methylaminoethanol instead of aminoethanol, the title compound is produced.

4'-(N-(GAMMA,DELTA-DIHYDROXYBUTYL)AMINOETHYL)-4',5'-DIETHYL-8-METHYLPSORALEN

In the same manner as given in the foregoing, but starting from 3,4-dihydroxybutylamine instead of aminoethanol and 4'-chloroethyl-4,5'-diethyl-8-methylpsoralen instead of 4'-chloromethyl-4,5',8-trimethylpsoralen, the title compound is produced.

In the same manner as given in the foregoing, other variations in selection of starting materials are productive of still other 4'-(N-hydroxyloweralkyl)aminoloweralkyl-4,5',8-loweralkylpsoralens within the scope of the invention in which one, two, three or all of the loweralkyl groups present in the compound are varied. As used herein, the term "loweralkyl" comprehends such straight or branched radicals or groups having one to eight carbon atoms, preferably one to four carbon atoms, inclusive, such as methyl, ethyl, propyl, isopropyl, butyl, and the like. When present in the 4' position as part of the (N-hydroxyloweralkyl)amino loweralkyl group, a loweralkyl group will also be substituted by one or more hydroxy groups, as illustrated by the foregoing examples, depending upon the exact aminoalkanol starting material employed.

PHARMACOLOGY

The biophotosensitization activity of the compounds of the present invention was determined by visual grading of erythemal response according to a modification of the procedure of Pathak and Fitzpatrick, J. Invest. Dermatol. 32, 509–518 (1959), entitled "Bioassay of Natural and Synthetic Furocoumarins (Psoralens)". (The psoralens are of course "linear" isomers of the furocoumarin family.) According to this bioassay of photosensitizing potency, erythema production on albino guinea pig skin is measured visually and the response accorded a gradation definition according to a 0, ∓, 1, 2, 3, and 4 scale. The modification employed involved variation of the time between administration of the test compound and exposure to ultraviolet light, thereby enabling measurement of times of onset and decline of the induced photosensitivity effect.

PROTOCOLS

Topical: Each drug is tested topically at a concentration of one percent (1%) in ethanolic solution. Test sites of one square centimeter of skin each receive one-tenth milliliter of a particular selected test solution thirty minutes prior to exposure to three joules of ultraviolet "A" radiation. Three species of fifteen in each group of guinea pigs are tested with each product to arrive at an average response designated "Reaction Intensity", which is determined by observation and grading 24 hours and 48 hours after administration.

Oral: Each drug is tested orally by administering a dosage of forty (40) mgm/kgm of body weight to groups of fifteen guinea pigs. The appropriate dosage for each animal is packed into a gelatin capsule and placed far back in the animal's pharynx. Swallowing is assisted by syringe delivery of three milliliters of water. The animals are not allowed to eat or drink six hours before and after administration of each product. The exposure to ultraviolet "A" radiation is at a dose of four joules per square centimeter at different times after administration, e.g., 10, 20, 30, 45, 60, 90, 120, 180, 240 minutes after administration. Readings and evaluations are carried out 48 hours post ingestion. When a particular product is exceptionally active in the test, the per os dosage may of course be halved or otherwise reduced.

Gradation: Responses are graded as follows:

0 No response; ± faint erythema; 1+ erythema; 2+ erythema and slight edema; 3+ erythema and intense edema; and 4' vesiculobullous reaction.

RESULTS

The compounds of the invention show erythematic topical activity as read at both 24 and 48 hours. They show oral activity as read at 48 hours which is outstanding, with effective maxima, early onset, and rapid decline in photosensitizing effect. The compound 4'-(N-beta-hydroxyethyl)aminomethyl)-4,5',8-trimethylpsoralen is particularly outstanding, dropping off to only faint erythema at 240 minutes, with an early onset of 3+ activity at 30 minutes and vesicubullous reaction at only 60 minutes. It is superior in photosensitizing maximum at 90 and 120 minutes when compared with 4'-aminomethyl-4,5',8-trimethylpsoralen, and in all respects superior to the control methoxsalen (8-methoxypsoralen) which moreover does not show a rapid decline, exhibiting a 2+ rating after 240 minutes.

Further outstanding performance was exhibited by the compound 4'-beta-hydroxyethoxymethyl-4,5',8-trimethylpsoralen, which showed immediate erythematic response at 30 minutes, effective photosensitizing activity at 60 and 90 minutes, being fully equal in activity to 4'-aminomethyl-4,5',8-trimethylpsoralen at 90 and 120 minutes, both compounds dropping off to only faint erythema at 240 minutes. This compound was approximately as effective orally as 8-methoxypsoralen, but superior in that it declined to only faint erythema at 240 minutes, whereas 8-methoxypsoralen retained a 2+ rating at 240 minutes.

The compounds of the invention show no oral toxicity, no animals dying at any of the dosage levels tested. In contrast, the compound 4'-aminomethyl-4,5',8-trimethylpsoralen shows a high order of oral toxicity, a large number of the animals receiving 40 mgm/kgm thereof dying during the period of their observation, the LD50 for that particular compound apparently being much less than this dosage level.

It is to be understood that the invention is not to be limited to the exact details of operation or exact compounds, compositions, methods, or procedures shown and described, as obvious modifications and equivalents will be apparent to one skilled in the art.

I claim:

1. 4'-R-4,5',8-triloweralkylpsoralen, wherein the R substituent on the 4' carbon atom is selected from the group consisting of hydroxyloweralkoxyloweralkyl and N-(hydroxyloweralkyl)aminoloweralkyl.

2. A compound of claim 1, which is 4'-hydroxyloweralkoxymethyl-4,5',8-trimethylpsoralen.

3. A compound of claim 2, which is 4'-beta-hydroxyethoxymethyl-4,5',8-trimethylpsoralen.

4. A compound of claim 1, which is 4'-(N-hydroxyloweralkyl)aminomethyl-4,5',8-trimethylpsoralen.

5. A compound of claim 4, which is 4'-(N-(beta-hydroxyethyl)aminomethyl)-4,5',8-trimethylpsoralen.

6. A pharmaceutical composition suitable for use in effecting photochemical sensitivity on the skin of a mammal comprising a photo-sesitizing amount of a compound of claim 1 and a pharmaceutical carrier therefor.

7. The composition of claim 6, wherein the compound is 4'-hydroxyloweralkoxymethyl-4,5',8-trimethylpsoralen.

8. The compound of claim 6, wherein the compound is 4'-beta-hydroxyethoxymethyl-4,5',8-trimethylpsoralen.

9. The composition of claim 6, wherein the compound is 4'-(N-hydroxyloweralkyl)-aminomethyl-4,5',8-trimethylpsoralen.

10. The compound of claim 6, wherein the compound is 4'-(N-(beta-hydroxyethyl)-aminomethyl)-4,5',8-trimethylpsoralen.

11. The method of effecting photochemical sensitivity on the skin of a mammal comprising the step of orally or topically administering to the said mammal an effective photosensitizing dose of a compound of claim 1.

12. The method of claim 11 wherein the compound is 4'-hydroxyloweralkoxymethyl-4,5',8-trimethylpsoralen.

13. The method of claim 11, wherein the compound is 4'-beta-hydroxyethoxymethyl-4,5',8-trimethylpsoralen.

14. The method of claim 6, wherein the compound is 4'-(N-hydroxyloweralkyl)-aminomethyl-4,5',8-trimethylpsoralen.

15. The method of claim 11, wherein the compound is 4'-(N-beta-hydroxyethyl)-aminomethyl)-4,5',8-trimethylpsoralen.

* * * * *

UNITED STATES PATENT AND TRADEMARK OFFICE
CERTIFICATE OF CORRECTION

PATENT NO. : 4,269,852
DATED : May 26, 1981
INVENTOR(S) : Kurt D. Kaufman

It is certified that error appears in the above—identified patent and that said Letters Patent is hereby corrected as shown below:

[56] References Cited, U.S. PATENT DOCUMENTS, under OTHER PUBLICATIONS, line 2; "Comet." should read -- Cosmet. -- (copy of the original document)

Col. 2, lines 52 & 53; "4'-(N-hydroxyloweralkyl-)aminomethyl-" should read -- 4'-(N-hydroxyloweralkyl)-aminomethyl- --

Col. 5, lines 20 & 21 "-DIHYDROXYBUTYL-)AMINOETHYL-4,5'-" should read -- -DIHYDROXYBUTYL)-AMINOETHYL-4,5'- --

Col. 7, line 21; "compound" (first occurrence) should read -- composition --

Col. 8, line 4; "compound" (first occurrence) should read -- composition --

Col. 8, line 17; "claim 6" should read -- claim 11 --

Col. 8, line 20, after "compound" insert -- is --
Col. 8, line 21; "4'-(N-beta-" should read -- 4'-(N-(beta- --

Col. 6, line 24; "4'" should read -- 4+ --

Signed and Sealed this

Eighth Day of September 1981

[SEAL]

Attest:

GERALD J. MOSSINGHOFF

Attesting Officer    Commissioner of Patents and Trademarks